United States Patent [19]

Widlund et al.

[11] Patent Number: 5,792,130
[45] Date of Patent: Aug. 11, 1998

[54] DIAPER WITH OPENING IN TOP SHEET

[75] Inventors: Urban Widlund, Mölnlycke; Anna Svernlöv, Kullavik, both of Sweden

[73] Assignee: Mölnlycke AB, Gothenburg, Sweden

[21] Appl. No.: 646,332

[22] PCT Filed: Dec. 8, 1994

[86] PCT No.: PCT/SE94/01178

§ 371 Date: Jun. 5, 1996

§ 102(e) Date: Jun. 5, 1996

[87] PCT Pub. No.: WO95/16418

PCT Pub. Date: Jun. 22, 1995

[30] Foreign Application Priority Data

Dec. 13, 1993 [SE] Sweden ............... 9304131-7

[51] Int. Cl.⁶ ............... A61F 13/15
[52] U.S. Cl. ............... 604/385.1; 604/385.2
[58] Field of Search ............... 604/378, 385.1, 604/385.2, 386, 389, 390, 395

[56] References Cited

U.S. PATENT DOCUMENTS

| | | | |
|---|---|---|---|
| 4,834,737 | 5/1989 | Khou | 604/385.2 |
| 5,062,840 | 11/1991 | Holt et al. | 604/385.1 |
| 5,269,775 | 12/1993 | Freeland et al. | 604/385.2 |
| 5,624,422 | 4/1997 | Allen | 604/385.2 |

FOREIGN PATENT DOCUMENTS

| | | |
|---|---|---|
| 0 357 298 | 3/1990 | European Pat. Off. . |
| 0 486 006 | 5/1992 | European Pat. Off. . |
| 2268073 | 1/1994 | United Kingdom ............... 604/385.1 |

*Primary Examiner*—Mark O. Polutta
*Attorney, Agent, or Firm*—Young & Thompson

[57] ABSTRACT

A diaper having a front part (12), a back part (14) and an intermediate crotch part (13) which includes an absorbent body unit (1) which is joined to a fluid-impermeable bottom sheet (7) and to a fluid-permeable top sheet (9) which lies proximal to the wearer's body in use and which includes an opening (15) situated in the back part and crotch part of the diaper and stretch-mounted elastic devices (20, 21), and which is not attached to the absorbent body unit at least within the region of the opening (15). The absorbent body unit (1) includes a main body (2) which is provided with a leg recess on respective sides thereof, and two side-bodies (3, 4) which are placed laterally outside the main body on respective sides thereof and in respective leg recesses. The absorbent body unit (1) is enclosed between the bottom sheet (7) and an inner casing sheet (8) made of fluid-permeable material, the sheets being mutually joined at parts which lie outside the absorbent body unit and carry stretch-mounted elastic elements (10, 11) along their respective side edges within at least the central part of the diaper. Each side-body (3, 4) has an arcuate edge on that side (22) thereof which lies proximal to a respective leg recess in the main body (2). The side-bodies are spaced from the main body (2); and the inner casing sheet (8) is joined to the bottom sheet (7) in those gaps that are formed in the leg recesses between the main body and the side-bodies.

9 Claims, 3 Drawing Sheets

DIAPER WITH OPENING IN TOP SHEET

CROSS-REFERENCES TO RELATED APPLICATIONS

This application is filed under 35 U.S.C. § 371 as the national stage application of International application PCT/SE94/01178, filed on Dec. 8, 1994, which designated the United States of America.

FIELD OF THE INVENTION

The present invention relates to a diaper having a front part, a back part and an intermediate crotch part which includes an absorbent body which is joined to a fluid-impermeable bottom sheet and to a fluid-permeable top sheet which lies proximal to the wearer's body in use and which includes an opening situated in the back part and crotch part of the diaper and stretch-mounted elastic devices, and which is not attached to the absorbent body at least within the region of said opening, wherein the absorbent body includes a main body which is provided with a leg recess on respective sides thereof, and two side-bodies which are placed laterally outside the main body on respective sides thereof and in respective leg recesses.

BACKGROUND OF THE INVENTION

One such diaper is known from EP-A2-0,486,006 and is intended to avoid irritation of the wearer's skin as a result of excrement or urine coming into contact therewith. According to this publication, this is achieved by deformation of the absorbent body into a basin-like shape as the elastic devices provided in the top sheet contract, at the same time as the top sheet is distanced from the bottom of the basin and forms an apertured basin lid or cover. One problem with diapers of this kind is that the opening or aperture in the top sheet must be so large and so positioned as to ensure that excrement from the wearer will fall down onto the absorbent body. If excrement lands on the top sheet, there is a serious risk of leakage and irritation of the skin. Another problem is one of constructing the diaper so that the diaper will be deformed appropriately as the top sheet is shortened by contraction of the elastic devices, and to prevent the whole of the absorbent body coming into abutment with the top sheet during the use of the diaper.

An object of the present invention is to solve or at least greatly reduce these problems.

SUMMARY OF THE INVENTION

This object is achieved in accordance with the invention with a diaper of the kind defined in the introduction which is characterized in that the absorbent body is enclosed between the bottom sheet and an inner fluid-permeable casing sheet, said sheets being joined mutually at parts which lie outside the absorbent body and carry stretch-mounted elastic elements along their side edges within at least the central part of the diaper; in that each side-body has an arcuate edge on the side thereof proximal to the leg recess of the main body; in that the side-bodies are spaced from the main body; and in that the inner casing sheet is joined to the bottom sheet in those gaps that are formed in the leg recesses between the main body and the side-bodies.

According to one preferred embodiment of the invention, the main body of the absorbent body includes an upper layer which lies proximal to the top sheet and a bottom layer which extends longitudinally at least along the leg recesses of the main body and has greater rigidity than the top layer.

The sides of the side-bodies that lie distal from the leg recesses in the main body also have arcuate edges and the side-bodies are made from an absorbent deformable material. When the diaper is held flat with elastic devices and elements stretched, the sides of the side-bodies distal from the main body will preferably have straight edges. In one variant, the circle-segmental side-bodies include a row of wedge-shaped recesses on the straight side thereof distal from the main body.

BRIEF DESCRIPTION OF THE INVENTION

The invention will now be described in more detail with reference to the accompanying drawings, in which FIG. 1 is a perspective schematic view of a first embodiment of an inventive diaper seen obliquely from above;

DETAILED DESCRIPTION OF THE INVENTION

Figure 1:
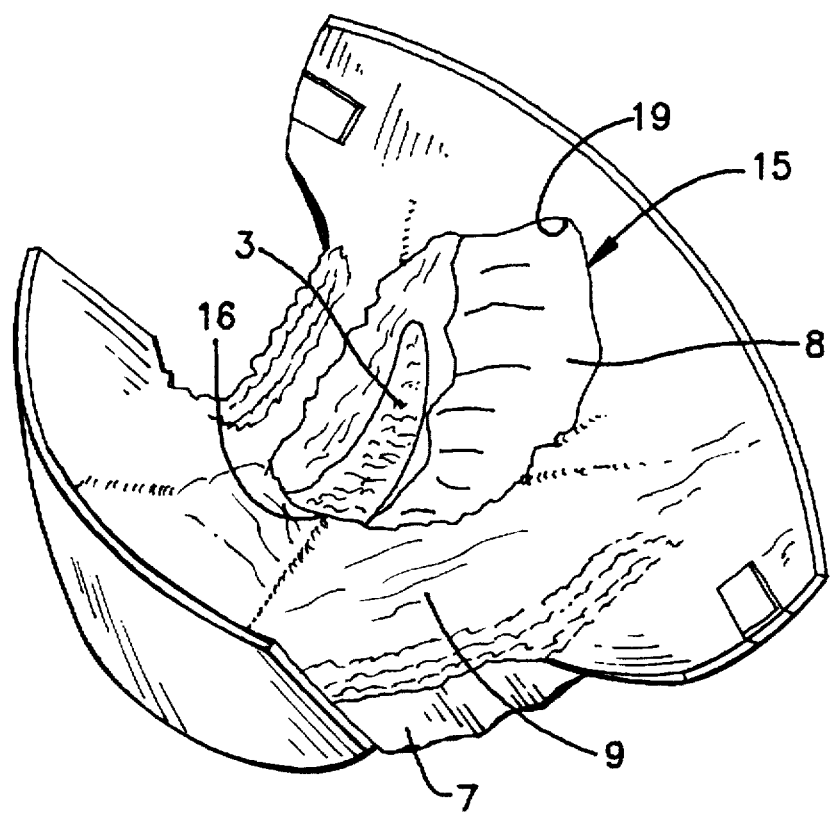

The diaper illustrated in FIGS. 1–4 includes an absorbent body unit 1 which is comprised of a main body 2 of hourglass configuration and two side bodies 3, 4. The main body 2 is comprised of two layers 5, 6 of which the upper layer 5, and also the side-bodies 3, 4, are comprised of air-laid cellulose fluff, whereas the bottom layer 6 includes an absorbent reel material of the kind described in Swedish Patent Application No. 9203445-3, which contains a dry formed sheet containing 5–100% cellulose fibres having a bulk density of between 0.2–1.0 g/cm$^3$ and a surface weight of between 30–2000 g/cm$^2$ and which is formed by compressing a web containing cellulose fibres without subsequent defibration and fluff forming. The reader is referred to the above-mentioned application for closer details of such reel material. As will be seen from FIG. 4, the layer 6 is rectangular in shape and extends only beneath part of the layer 5. It will be understood, however, that the layer 6 may have other shapes than rectangular, for instance the layer 6 may have an hourglass shape, T-shape, etc., conforming to the layer 5. The layer 6 may also be given a greater extension longitudinally, for instance it may be given the same form and extension as the layer 5. It is not necessary that the layer 6 be comprised of absorbent material, even if this is to advantage, and it is also possible to exclude this layer entirely when the remainder of the absorbent body has the desired stiffness or rigidity.

The absorption body unit 1 is enclosed between an outer casing sheet or backing sheet 7 of liquid-impermeable material, such as polyethylene plastic for instance, and an inner liquid-permeable casing sheet 8, which is preferably comprised of nonwoven material. The inner sheet 8 and the backing sheet 7 are preferably of identical shape and are joined together at parts which lie outside the absorbent body 1. As will best be seen from FIG. 4, the side-bodies 3, 4 are positioned laterally slightly outside the main body 2 and the casing sheets 7, 8 are mutually joined in the gaps between the main body and the side bodies.

Figure 2:
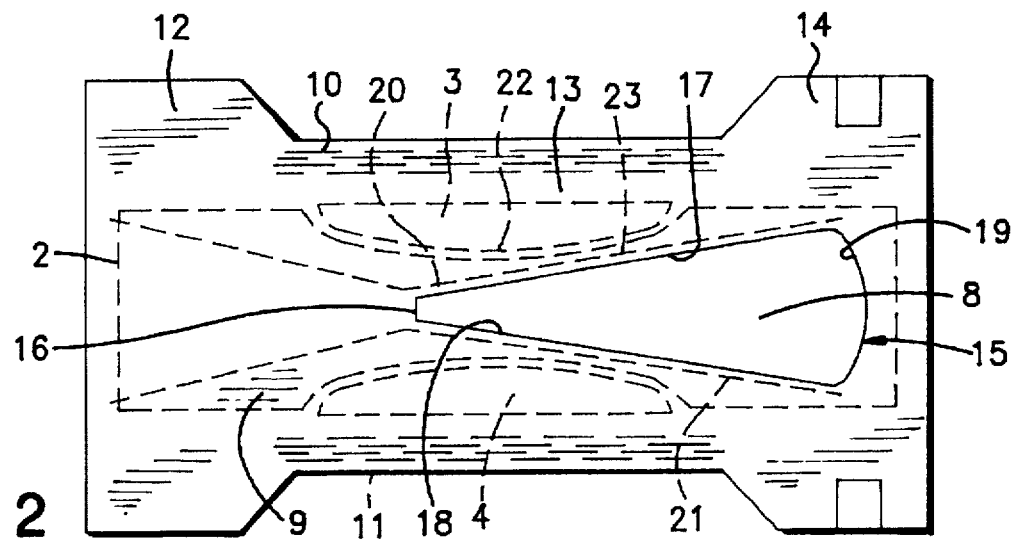
FIG. 2 illustrates the diaper of FIG. 1 schematically from above and shows the diaper in a flat state.
Figure 3:
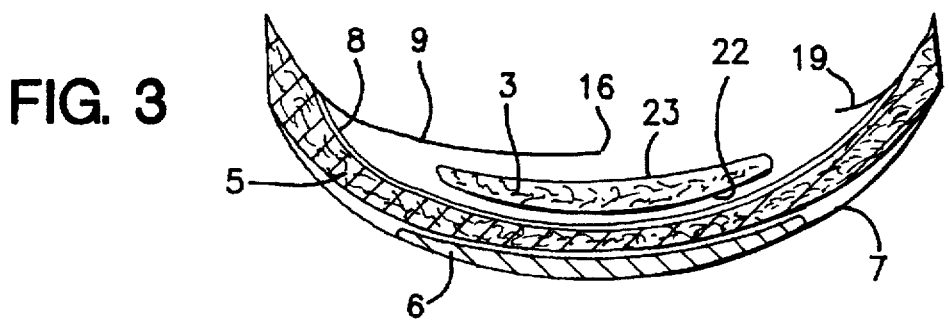
FIG. 3 is a schematic cross-sectional view of the diaper illustrated in FIG. 1.

The diaper also includes a top sheet 9 whose shape is identical to the shapes of the casing sheets 7, 8 and which is fastened to said sheets along diaper edge parts, so that the top sheet will be generally free from the absorbent body 1, i.e. generally unattached thereto. As illustrated in FIGS. 1 and 2, the diaper includes leg elastic in the form of elastic devices 10, 11 which extend along the side edges of the crotch part 13 and along parts of the front diaper part 12 and the back diaper part 14. In the illustrated embodiment, the elastic devices are comprised of four elastic threads which are attached in a stretched state between the top sheet 9 and the inner casing sheet 8 and fastened to said sheets. It will be understood that the number of leg elastics used may be greater or fewer than four threads, and that other types of elastic devices may be used, such as elastic bands or ribbons, bands of film material that has elastic properties, etc. It will also be understood that the elastic devices 10, 11 may be mounted between the bottom sheet 7 and the inner casing sheet 8 instead.

An opening 15 is formed in the top sheet 9 symmetrically in relation to the longitudinal direction of the diaper. The front edge 16 of this opening is located between the wetting point and the excretion point. By wetting point is meant that region of the diaper within which urine discharged by the wearer is expected to be deposited when the diaper is correctly positioned on the wearer, and by excretion point is meant correspondingly that region of the diaper within which faeces will be deposited on a correctly positioned diaper, i.e. those regions which lie opposite to the external urethra orifice and the anus of the wearer, while taking into consideration normal variations in the wearer's anatomy within the size ranges of the wearer for which the used diaper is dimensioned. The side edges 17, 18 of the opening 15 extend divergently away from one another in a direction towards the back diaper part, and the rear edge 19 of the opening is arcuate in shape and located in the back diaper part at a short distance from the rear end of the absorbent body.

Two elastic threads 20, 21 are fastened in a stretched state to the top sheet 9 and extend from the forward part of the front diaper part 12 to the rear part of the back diaper part 14. The threads 20, 21 extend mutually convergent from the front part 12 to the forward edge 16 of the opening 15 and then extend along the side edges 17, 18 of the opening generally on the same level as the rear edge 19 of the opening. In the illustrated embodiment, the threads 20, 21 are mounted between the top sheet and narrow strips of nonwoven material (not shown) which are fastened to the threads and the top sheet with the aid of glue or by some other suitable means. In the illustrated embodiment, the strips are disposed along the full length of the threads and are thus fastened to the top sheet along the whole of its length. This is not absolutely necessary, however, since the desired function can be achieved sufficiently well when the threads are fastened to the top sheet at their respective ends and on both sides of the front edge.

In one variant of the invention, the nonwoven strips are fastened to the top sheet at their respective edges so as to form guide passages for elastic threads extending therethrough. In the case of this embodiment, it is sufficient to fasten the threads to the top sheet at the ends of the passages. For instance, if the nonwoven strips extend along the full length of the elastic threads it is sufficient to fasten the ends of the threads to the tops sheet. It is preferred that the threads will extend freely in the guide passages, at least along the edges of the opening 15. When the top sheet lacks the provision of guide passages forwardly of the opening 15, the nonwoven strips can be formed unitary with the top sheet, by folding said top sheet in conjunction with cutting out the opening 15. In this case, the provision of separate nonwoven strips in front of the opening can be omitted, in which case the threads will lie freely between their forward top sheet attachment points and the ends of the passages at the forward edge of the opening. As will be understood, it is also possible to fasten the threads to the top sheet along the whole of that part thereof which extends in front of the opening, for instance by attaching separate nonwoven strips.

FIG. 2 illustrates the diaper in a flat state, i.e. the state in which the diaper is found during manufacture, in which the diaper is held stretched against the action of the spring force exerted by the elastic devices. When the finished diaper is released from its stretched state, the elastic devices 10, 11, 20 and 21 strive to contract to a tensionless or relaxed state, therewith deforming the diaper to the shape illustrated in FIGS. 1 and 3.

Contraction of the elastic threads 20, 21 causes the top sheet to gather together and therewith shorten. In order to allow this shortening of the top sheet to take place, the main body 2 of the absorbent body unit 1 is curved at the same time as the side bodies 3, 4 are swung upwards about hinge means formed by the casing sheets 7, 8, these sheets being joined in the gaps defined between respective side bodies 3, 4 and the main body 2. Thus, the elastic threads 20, 21 are instrumental in maintaining the top sheet 9 in spaced relationship with the absorbent body 1. The provision of the bottom layer 6, which is stiffer than the layer 5 of the absorbent body 1, ensures that the main body 2 will not be folded when the top sheet is gathered, but obtains an even curvature.

It is mentioned in this respect that FIG. 1 illustrates the diaper when no load is exerted thereon, and thus not when the diaper is worn. As will be understood, the shape adopted by a diaper when in use will depend on the anatomy of the wearer, and the diaper is so dimensioned that the elastic threads 20, 21 will normally be stretched slightly as the diaper is placed in position on the wearer. However, the length of the diaper is such that a large part of the fold or gather in the top sheet will remain after having put on the diaper, so that the absorbent body will be located at a distance from the top sheet along a greater part of its extension, even after having put the diaper on.

Thus, there is found between the absorbent body and the top sheet a space in which excrement i.e. faeces is kept out of contact with the skin. Furthermore, it must be ensured that excrement is deposited in this space and not on the top sheet, and it will therefore be understood that the size and positioning of the opening are of decisive importance, particularly with regard to the excrement point. It has been found that the distance between the side edges 17, 18 of the opening should be at least 3 cm at the excrement point, and that the front edge of the opening 15 should lie at least 1 cm and preferably 2 cm forwardly of the front edge 16, and that the front edge 16 should be at least 2 cm long. Because the elastic threads 20, 21 exert a spring force in both the longitudinal and transverse directions of the diaper when the diaper is worn, the front edge of the opening 15 and its side edges 17, 18 will be stretched outwardly so as to ensure that the aforesaid distances are retained when the diaper is in use. In order to achieve a high outward tensioning effect, the ends of the threads 20, 21 will preferably lie on the same level as the side edges of the absorbent body 1 essentially in a lateral direction.

In addition to gathering together the top sheet 9, the elastic threads 20, 21 also have a sealing function by lying sealingly against the wearer's body when the diaper is worn. This greatly reduces the risk of discharged urine running along the top sheet instead of passing through said sheet and being absorbed by the absorbent body in the manner intended. The fact that the elastic threads extend along the side edges of the opening also greatly reduce the risk of the position of the opening 15 being changed as a result of external forces on the diaper, for instance as the wearer of the diaper moves. An added advantage is that when the absorbent body is subjected to an external load and subsequently pressed towards the body of the wearer, it is more difficult for excrement to seep over the edges of the opening 15 and onto the top sheet 9. In order to obtain these sealing functions, it has been found that the distance between the side edges 17, 18 of the opening 15 at the centre of the excrement point should not exceed 6 cm and will preferably be smaller than 5 cm. The length of the front edge 16 of the opening 15 will preferably not exceed 4 cm.

From the aspect of absorption, the side bodies 3, 4 are not joined to the remainder of the absorbent body 1 and form safety bodies which absorb fluid when the main body 2 becomes saturated or is unable to absorb discharged fluid for some reason or another. In addition to this function, the side bodies also contribute to the stability of the basin that is formed when the top sheet is gathered together and prevent the main absorbent body in its entirety coming into abutment with the wearer's body when the diaper is subjected to an external load, as will be described below.

Figure 4:
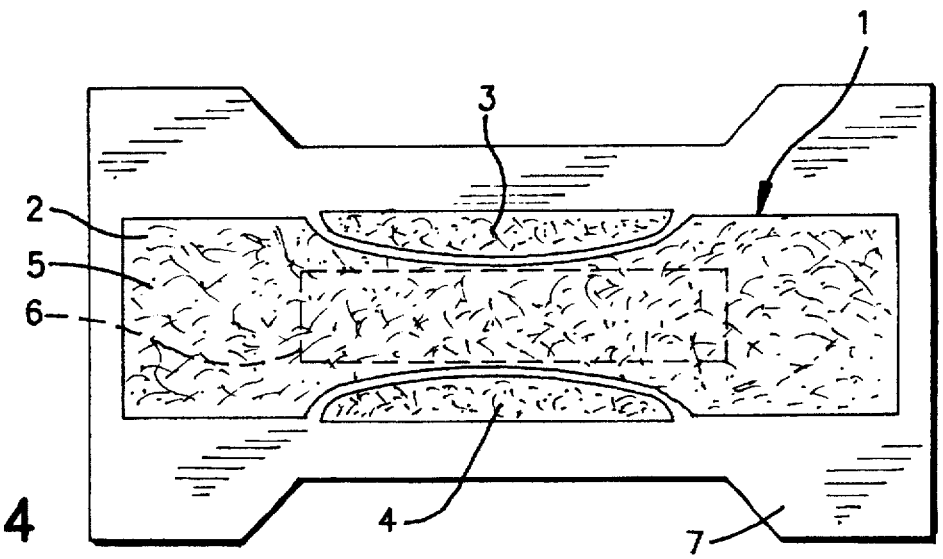
FIG. 4 is a view corresponding to the view in FIG. 2 showing the bottom sheet and the absorbent body of the diaper illustrated in FIG. 1.
Figure 5:
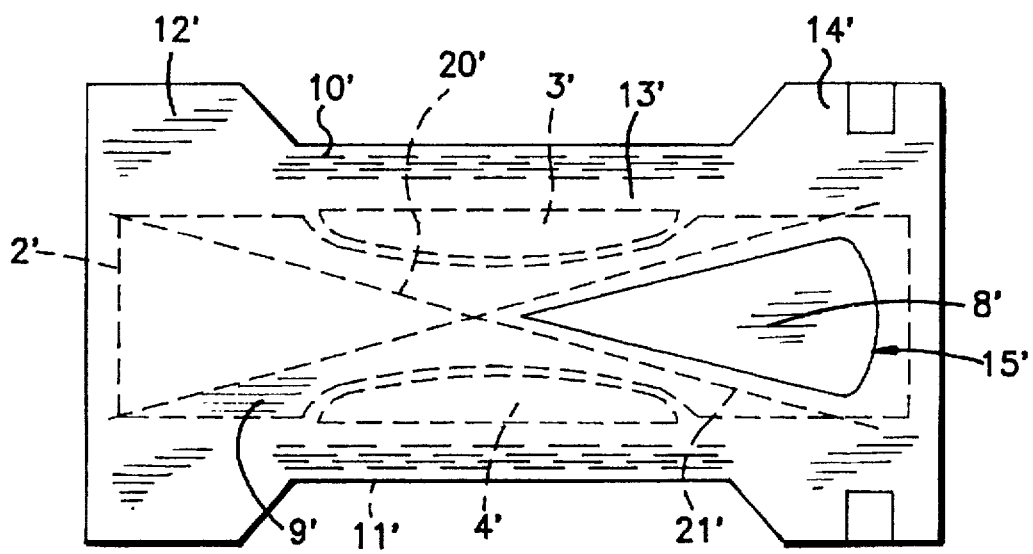
FIG. 5 is a view corresponding to the view in FIG. 2 and illustrates a second embodiment of an inventive diaper.

FIG. 5 illustrates a second embodiment of an inventive diaper in a view corresponding to the view of FIG. 2. Diaper components corresponding to the FIG. 2 embodiment have been identified with the same reference signs to which a prime has been added. In the case of the diaper illustrated in FIG. 5, the elastic threads 20', 21' cross one another in front of the opening 15' in the top sheet 9', and the opening is terminated forwardly in a point. The opening 15' thus has a punctiform front edge. In other respects, the diaper illustrated in FIG. 5 has the same construction as the diaper illustrated in FIGS. 1-4.

An extremely good sealing function can be achieved by the top sheet 9' as a result of the mutually crossing threads 20',21'. The point of intersection of the elastic threads 20', 21' shall lie between the wetting point and the excrement point and the same requirements as those placed on the diaper according to FIGS. 1-4 with regard to the distance between the side edges of the opening 15 at the excrement point also apply to the opening 15'. Accordingly, the point of intersection will lie relatively close to the wetting point, meaning that the illustrated embodiment cannot be worn readily by males, since space must be found between the elastic threads 20', 21' to accommodate the scrotum. Naturally, it is possible within the scope of the present invention to modify the extension of the threads within the region of the wetting point so as to prepare room for the scrotum.

When the diaper is worn, the absorbent body 1 can be likened to a flat-bottom boat or punt, where the main body 2 forms the bottom and the side-bodies 3, 4 form the freeboard of the "punt". Thus, when the diaper is worn, that side 22 of the side-bodies 3, 4 which lies proximal to the main body, or in other words the underside 22, shall have a curvature which corresponds to the curved shape that the main body shall take in order to form a suitable space between the absorbent body and the top sheet, which when the diaper is worn conforms to the shape of the wearer's body. The upper side 23 of the side-bodies shall thus have a smaller curvature which corresponds to the curvature of the wearer's anatomy.

Side-bodies 3, 4 which fulfil these requirements are obtained with the illustrated embodiments of the invention by giving the undersides 22 of the side-bodies an initial appropriately curved form and by manufacturing the same from a relatively soft and deformable material. As the elastic devices of the diaper illustrated in FIGS. 1-4 contract, the diaper will pass from the flat state illustrated in FIG. 4 to the state illustrated in FIG. 1. In this respect, contraction of the leg elastic devices 10, 11 causes the side-bodies 3, 4 to swing upwards around their hinges, formed by those parts of the layers 7, 8 joined in the gaps between the main body 2 and the side-bodies, and also deforms the upper sides 23 of the side-bodies into a curved shape. Contraction of the elastic threads 20, 21 in the top sheet 9 does not affect the side-bodies to any great extent, but merely causes the main body 2 to curve. Consequently, the invention is not restricted to a top sheet which includes elastic threads arranged in the patterns illustrated in FIGS. 2 and 5, but can be applied with all diapers provided with elastic devices that create folds or puckers in the top sheet, so that the tops sheet will be distanced from the absorbent body.

When a diaper is worn by the user, the side-bodies prevent external loads on the diaper, at least within the crotch part, from pressing the main body into abutment with the top sheet and ensure that a given storage space will always remain. Because the underside of the side-bodies conform generally to the curved shape of the main body and the upper side of said side-bodies conform to the shape of the wearer, deformation due to external loads, for instance as the wearer of the diaper sits down, takes place essentially by compression and/or inward swinging of the side-bodies and the change in curvature of the main body. Furthermore, as a result of the described configuration of the side-bodies, the pressure at which the side-bodies abut the wearer's body will be uniformly distributed both in the absence of load on the diaper and when the diaper is subjected to external forces, therewith providing a comfortable diaper and reducing the risk of the diaper chafing against the skin of the wearer within the region of the side-bodies.

Figure 6:
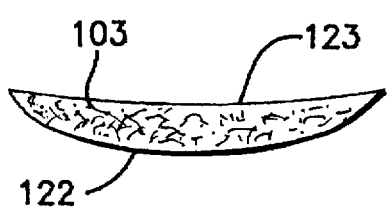
FIGS. 6 and 7 illustrate different embodiment of side-bodies suitable for use in an inventive diaper.

FIG. 6 illustrates an embodiment of a side-body 103 which differs from the side-bodies illustrated and described above, in that the side-body is initially given a crescent-like shape with a curved upper side 123, this curve corresponding generally to the shape of the wearer's body, and an underside 122 which has a curvature corresponding to the desired curvature of the main body, as in the earlier case.

Figure 7:
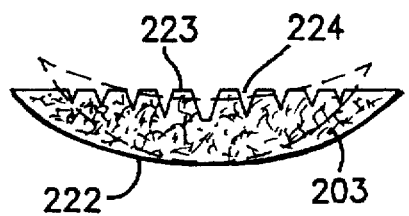

FIG. 7 illustrates another embodiment of a side-body 203 which has a row of wedge-shaped recesses 224 formed in its upper part. When a side-body of this kind is used in a diaper which in other respects is constructed in the same manner as the diaper illustrated in FIGS. 1-4, contraction of the leg elastic will deform the side-body to the shape illustrated in broken lines in FIG. 7.

Figure 8:
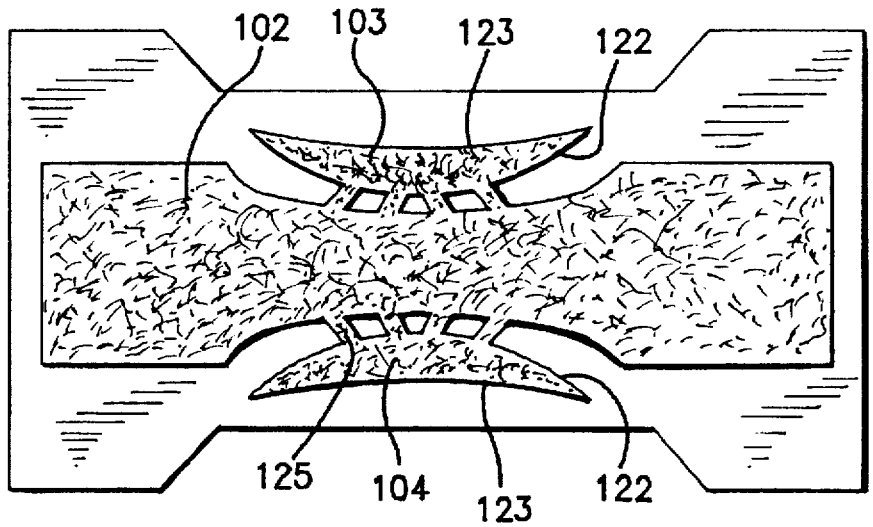
FIG. 8 is a view similar to the view in FIG. 4 and illustrates an inventive absorbent body provided with side-bodies according to FIG. 6.

FIG. 8 is a view similar to the view of FIG. 4 and illustrates a third embodiment of an inventive diaper. This embodiment differs from the earlier described embodiments primarily in that crescent-shaped side-bodies 103, 104 having curved upper sides are used instead of side-bodies that have straight upper sides. The undersides 122 of the side-bodies 103, 104 also have a greater curvature than the leg recesses of the main body 102, which means that the gap between main body and side-bodies will have a varying width. It will be seen that when the top sheet of such a diaper is gathered together, the basin that is formed by the main body 102 and the upraised side-bodies 103, 104 will be deeper than the basin that is formed in the diaper illustrated in FIG. 1. The depth of the basin formed can be varied by varying the curvature of the underside of the side-bodies.

From an absorption aspect, the side-bodies 103, 104 of the FIG. 8 embodiment may be joined to the main body by four narrow strings or bridges 125 of absorbent material, through which fluid can be drawn by suction from the main body 102 by the side-bodies 103, 104 when the main body is saturated in the sensitive crotch part.

It will be noticed that the term "diaper" as used in the present document is intended to include so-called pants-type diapers and incontinence guards for people suffering double incontinence.

It will be understood that the illustrated and described embodiments can be modified within the scope of the present invention. For example, the side-bodies can be made of a stiffer material, for instance the same material as the bottom layer 6 of the main body or tissue, when the upper sides of said side-bodies are formed in accordance with the embodiments of FIGS. 6 and 7 rather than said upper sides being straight initially. It is not necessary that the side-bodies be made of an absorbent material, even though this is preferred. Naturally, the upper part of the side-bodies may conceivably be formed from a softer material than the bottom part. The side-bodies need not extend beyond the outer side extremity of the main body, and the outer side edges of said side-bodies may extend flush with said outer side extremity or may even terminate short thereof. The invention is therefore restricted solely by the content of the following claims.

We claim:

1. A diaper extending in a longitudinal direction and comprising:

a front part, a back part, and an intermediate crotch part, an absorbent body unit joined to a fluid-impermeable bottom sheet, and to a fluid-permeable top sheet which lies proximal to a wearer's body in use, said top sheet including an opening situated in the back and crotch parts of the diaper, and stretch-mounted elastic devices, said top sheet being unattached to the absorbent body unit at least within the region of the opening, said absorbent body unit including a main body provided with a leg recess on respective sides thereof, and two side-bodies placed laterally outside the main body on respective sides thereof and in respective leg recesses, said absorbent body unit being enclosed between the bottom sheet and a fluid-permeable inner casing sheet, said bottom and inner casing sheets being mutually joined at parts which lie outside the absorbent body unit and carry stretch-mounted elastic elements along their respective side edges within at least a central part of the diaper; each side-body having an arcuate edge on that side thereof which lies proximal to a respective leg recess in the main body, the side-bodies being spaced from the main body, and the inner casing sheet being joined to the bottom sheet in those gaps that are formed in the leg recesses between the main body and the side-bodies.

2. A diaper according to claim 1, wherein the main body of the absorbent body unit includes an upper layer which lies proximal to the top sheet and a lower layer which longitudinally extends at least along the leg recesses of the main body, said lower layer having a greater rigidity than the upper layer.

3. A diaper according to claim 1, wherein those sides of the side-bodies which lie distal from the leg recesses of the main body also have arcuate edges.

4. A diaper according to claim 3, wherein the side-bodies are made of deformable material.

5. A diaper according to claim 4, wherein when the diaper is held flat with the elastic devices and elastic elements held stretched, the sides of the side-bodies distal from the main body have straight edges.

6. A diaper according to claim 1, wherein the side-bodies include a row of wedge-shaped recesses on that side thereof distal from the main body.

7. A diaper according to claim 4, wherein when the diaper is held flat with the elastic devices and elastic elements held stretched, the side-bodies have a crescent-like shape, and respective sides of the side-bodies that lie proximal to and distal to the main body have a curved edge.

8. A diaper according to claim 1, wherein the side-bodies are made from absorbent material.

9. A diaper according to claim 8, wherein the side-bodies are joined to the main body by bridges of absorbent material.

* * * * *